United States Patent [19]

Holden

[11] 4,053,468
[45] Oct. 11, 1977

[54] PROCESS FOR PREPARING 7-OXO CEPHALOSPORINS AND 6-OXO PENICILLINS

[75] Inventor: Kenneth G. Holden, Haddonfield, N.J.

[73] Assignee: SmithKline Corporation, Philadelphia, Pa.

[21] Appl. No.: 661,230

[22] Filed: Feb. 25, 1976

[51] Int. Cl.$^2$ .......................................... C07D 501/04
[52] U.S. Cl. .............................. 544/30; 260/306.7 C; 544/26
[58] Field of Search .......... 260/239.1, 243 C, 306.7 C

[56] References Cited
PUBLICATIONS

Corey et al., J. Am. Chem. Soc. 91: 1429 (1969).
Calo et al., J. Chem. Soc. Perkin I: 1652 (1972).
Yanagisawa et al., Tetrahedron Lett. 31: 2705 (1975).
Lo et al., J. Amer. Chem. Soc. 94: 8253 (1972).

*Primary Examiner*—Gerald A. Schwartz
*Attorney, Agent, or Firm*—Janice E. Williams; William H. Edgerton; Alan D. Lourie

[57] ABSTRACT

A process for preparing 7-oxo cephalosporins and 6-oxo penicillins by reaction of a 7-amino cephalosporin or 6-amino penicillin with a carbonyl-containing oxidizing agent is disclosed.

15 Claims, No Drawings

PROCESS FOR PREPARING 7-OXO CEPHALOSPORINS AND 6-OXO PENICILLINS

This invention relates to a novel process for preparing 7-oxo cephalosporin and 6-oxo penicillin compounds which are useful as starting materials for the preparation of 7β-hydroxy cephalosporins and 6β-hydroxy penicillins which are intermediates for the preparation of biologically active 7β-acyloxy cephalosporins and 6β-acyloxy penicillins. More specifically, the 7-oxo cephalosporins and 6-oxo penicillins are prepared by reaction of a 7-amino cephalosporin or 6-amino penicillin (I) with a carbonyl-containing oxidizing agent, in the presence of a solvent, as shown below:

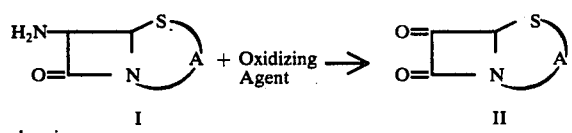

wherein:

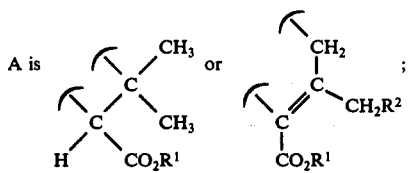

$R^1$ is hydrogen or an easily removable ester protecting group; and $R^2$ is hydrogen, acetoxy or SHet where Het is a five or six membered heterocyclic ring containing carbon and one to four atoms selected from the group consisting of N, O and S, each such ring being unsubstituted or substituted with one or two groups selected from alkyl, alkoxyalkyl and trifluoromethyl, each alkyl or alkoxy group having from one to four carbon atoms.

The term "easily removable ester protecting group" is one which has acquired a definite meaning within the cephalosporin and peptide art. Many such groups are known which are used to protect the carboxyl group during subsequent chemical reactions and are later removed by standard methods to give the free carboxylic acid. Known ester protecting groups include 2,2,2-trichloroethyl, tertiary alkyl of from four to six carbon atoms, tertiary alkenyl of from five to seven carbon atoms, tertiary alkynyl of from five to seven carbon atoms, alkanoylmethyl of from two to seven carbon atoms, N-phthalimidomethyl, benzoylmethyl, halobenzoylmethyl, methylbenzoylmethyl, methanesulfonylbenzoylmethyl, phenylbenzoylmethyl, benzyl, nitrobenzyl, methoxybenzyl, benzyloxymethyl, nitrophenyl, methoxyphenyl, benzhydryl, trityl, trimethylsilyl, triethylsilyl and the like. The choice of an ester protecting group is well within the ability of one skilled in the art. Factors which are considered include the subsequent reaction conditions the group must withstand and the conditions desired for removing the protecting group. Because the novelty of this invention lies within the process for preparing the nucleus II, the choice of a protecting group is not critical to the invention.

Preferably, $R^1$ is an easily removable ester protecting group. Preferred $R^2$ groups are hydrogen, acetoxy and SHet where Het is unsubstituted or methyl substituted 1,2,3-triazolyl, 1,2,4-triazolyl, 1,2,3,4-tetrazolyl, 1,3,4-oxadiazolyl, 1,3,4-thiadiazolyl or 1,2,4-thiadiazolyl.

The 7-oxo cephalosporins or 6-oxo penicillins of formula II where $R^1$ is hydrogen are also prepared by hydrolysis, for example with acid, of the corresponding 7-oxo cephalosporins or 6-oxo penicillins where $R^1$ is an easily removable ester protecting group. Such acids are capable of forming salts with, for example, the alkali metals such as sodium or potassium, the alkaline earth metals such as calcium or with the ammonium cation.

The process of this invention is carried out by reaction of a 7-amino cephalosporin or 6-amino penicillin of formula I with a carbonyl-containing oxidizing agent, preferably in equimolar amounts, in the presence of a non-hydroxylic solvent. Examples of carbonyl-containing oxidizing agents which may be employed in the process of this invention are mesitylglyoxal, 3-nitromesitylglyoxal, 3,5-dinitromesitylglyoxal, benzothiazole-2-carboxaldehyde, 6-nitrobenzothiazole-2-carboxaldehyde, 3,5-di-i-propyl-1,2-benzoquinone, 3-methyl-5-i-propyl-1,2-benzoquinone, tetrachloro-1,2-benzoquinone, tetrabromo-1,2-benzoquinone, 2,6-di-t-butyl-1,4-benzoquinone and, preferably, 3,5-di-t-butyl-1,2-benzoquinone. It will be appreciated that other aldehyde and quinone oxidizing agents which are useful in effecting conversion of a cephalosporin 7-amino or penicillin 6-amino group to a 7-oxo or 6-oxo group, respectively, be recognized as equivalent to the carbonyl-containing oxidizing agents mentioned above and encompassed within the spirit and scope of this invention.

Advantageously, the reaction is carried out in the presence of a non-hydroxylic solvent, with solvents such as tetrahydrofuran, dioxane, chloroform, methylene chloride, carbon tetrachloride, benzene, toluene, xylene, ethyl acetate, acetonitrile, dimethylformamide, dimethylsulfoxide and ether being preferred, and in the presence of a dehydrating agent such as magnesium sulfate or molecular sieves at a temperature of from about 0° C. to the reflux temperature of the solvent being used, viz. from about 0° C. to about 190° C., preferably from about 0° C. to about 25° C., for from about 1 to about 72 hours, from about 12 to about 72 hours being preferred. Alternatively, azeotropic removal of water may be employed in place of the addition of a mild dehydrating agent as described above; of course, the reaction is then preferably carried out at the reflux temperature of the solvent being used. In addition, a base catalyst such as a tertiary amine may be employed to assist rearrangement of the initially formed condensation product (Schiff's base) to the final product.

Preferably, the reaction mixture is worked up by first removing the dehydrating agent, when used, by filtration and then treating the solution with aqueous acid, for example oxalic or hydrochloric acid, to hydrolyze the rearranged Schiff's base. The product II, is isolated by extraction into an organic solvent. When $R^1$ is an ester group, the product II may be hydrolyzed, for example with trifluoroacetic acid, to give the corresponding compound of formula II where $R^1$ is hydrogen. The product compounds are purified by standard chromatographic or crystallization methods which are well known to the art.

Oxidation of primary amines to ketones using carbonyl-containing oxidizing agents has been reported by Corey and Achiwa, *J. Amer. Chem. Soc.* 91:1429 (1969), and Caló et al., *J. Chem. Soc.* Perkin I:1652 (1972), for alkylamines, cycloalkylamines, benzhydrylamine, benzylamine, phenyl substituted alkylamines and 2-exo-bornylamine. Yanagisawa et al., *Tetrahedron Lett.* 31:2705 (1975), describe the reaction of 3,5-di-t-butyl-4-hydroxybenzaldehyde and diphenylmethyl 7-aminocephalosporanate followed by oxidation with lead dioxide to give a Schiff base which is used directly to prepare 7α-methoxycephalosporins without hydrolysis to the 7-oxo compound. Preparation of a 6-oxo penicillin by oxidation of the corresponding 6α-hydroxy compound is described by Lo and Sheehan, *J. Amer. Chem. Soc.* 94:8253 (1972). No examples of oxidation of a cephalosporin 7-amino group or a penicillin 6-amino group to the corresponding 7-oxo or 6-oxo compound are believed to have been described.

The 7-oxo cephalosporin and 6-oxo penicillin compounds prepared by the process of this invention are useful in the preparation of 7β-acyloxy cephalosporins and 6β-acyloxy penicillins which exhibit antibacterial activity. For example, reduction of a 7-oxo cephalosporin or a 6-oxo penicillin of formula II with, for example, a metal hydride reducing agent such as sodium borohydride according to standard procedures gives the corresponding 7β-hydroxy cephalosporin or 6β-hydroxy penicillin compound which is converted to a 7β-acyloxy cephalosporin or 6β-acyloxy penicillin via well-known esterification methods, for example by reaction of a 7β-hydroxy cephalosporin or 6β-hydroxy penicillin with an appropriate acid or other esterifying agent with subsequent removal of any protective groups present. When $R^2$ of the 7β-hydroxy compound is acetoxy, displacement with a heterocyclic thiol of the formula HSHet where Het is defined as above gives the corresponding cephalosporins where $R^2$ is SHet. This displacement may be also carried out on the 7-oxo compound with subsequent reduction of the oxo group as previously described. These 7β-hydroxy and 7β-acyloxy cephalosporins are described in application Ser. No. 588,096; a 6β-acyloxy penicillin is described by Sheehan and Lo, *J. Org. Chem.* 38:3227 (1973).

Often, the 7-oxo cephalosporin and 6-oxo penicillin compounds of formula II are isolated in a hydrated form, which may be represented as follows:

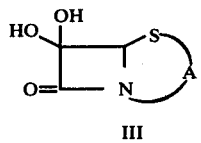

III where A is defined as above. Formation of any and all such hydrated forms of the product II are intended to be included within the scope of the process of this invention described above. The hydrates may be converted to the 7-oxo or 6-oxo compounds by, for example, heating in vacuo.

The following examples illustrate the invention but are not to be construed as limiting the scope thereof. Temperatures are in degrees Centigrade (°C.) unless otherwise indicated.

EXAMPLE 1

7-Oxodesacetoxycephalosporanic acid t-butyl ester

A solution of 13.5 g. (50 mmol.) of 7-aminodesacetoxycephalosporanic acid t-butyl ester and 11.0 g. (50 mmol.) of 3,5-di-t-butyl-1,2-benzoquinone in 150 ml. of tetrahydrofuran containing 20 g. of 5A molecular sieves was maintained at 4° for 72 hours. The reaction mixture was filtered, 15 g. of oxalic acid and 50 ml. of water were added to the filtrate and the solution was allowed to stand at 4° for 12 hours. The tetrahydrofuran was evaporated and the aqueous residue was partitioned between benzene and water (1:1). The insoluble material was removed by filtration, the layers were separated and the organic phase was diluted with hexane and extracted with water. Sodium chloride solution was added to the combined aqueous phases and they were extracted with ether. The ether extract was dried and evaporated to near dryness. Addition of benzene and hexane containing water induced crystallization of 7-oxodesacetoxycephalosporanic acid t-butyl ester hydrate. Heating the crystalline hydrate at 56° in vacuo gave the title compound as an oil.

$C_{12}H_{15}NO_4S \cdot 0.75 H_2O$: Calculated: 50.96% C; 5.88% H; 4.95% N; 11.34% S Found: 50.94% C; 5.68% H, 4.82% N; 11.06% S

EXAMPLE 2

7-Oxocephalosporanic acid t-butyl ester

A solution of 3.28 g. (10 mmol.) of 7-aminocephalosporanic acid t-butyl ester and 2.20 g. (10 mmol.) of 3,5-di-t-butyl-1,2-benzoquinone in 50 ml. of tetrahydrofuran containing 5 g. of 5A molecular sieves was maintained at 4° for 12 hours. The reaction mixture was worked up as described in the procedure of Example 1 to give 7-oxocephalosporanic acid t-butyl ester hydrate. Heating the hydrate at 56° under vacuum gave the title compound as an oil.

$C_{14}H_{17}NO_6 \cdot . H_2O$: Calculated: 48.69% C; 5.55% H; 4.06% N; Found: 48.70% C; 5.76% H; 3.89% N

EXAMPLE 3

7-Oxocephalosporanic acid

A solution of 0.15 g. (0.4 mmol.) of 7-oxocephalosporanic acid t-butyl ester in 20 ml. of trifluoroacetic acid-methylene chloride (1:4) containing 0.1 g. of anisole is allowed to stand at ambient temperature for 2 hours. The solvent is removed by evaporation at reduced pressure below ambient temperature. Trituration of the oily residue with wet ether gives a precipitate of 7-oxocephalosporanic acid hydrate. The title compound is obtained from the hydrate as described above.

EXAMPLE 4

7-Oxodesacetoxycephalosporanic acid

A solution of 2.14 g. (10 mmol.) of 7-aminodesacetoxycephalosporanic acid and 2.20 g. (10 mmol.) of 3,5-di-t-butyl-1,2-benzoquinone in 75 ml. of acetonitrile containing 1.4 ml. (10 mmol.) of triethylamine and 5.0 g. of anhydrous magnesium sulfate is maintained at 4° for 20 hours. Oxalic acid (5.0 g.) and 15 ml. of water are added and the resulting solution is allowed to stand for 16 hours at 4°. After removing most of the solvent under reduced pressure, the residue is partitioned between aqueous sodium bicarbonate solution and ethyl acetate. The aqueous phase is washed with another portion of ethyl acetate and is then acidified to pH 3.5 with concentrated phosphoric acid. The acid solution is extracted with ethyl acetate and the extract is evaporated to dryness to give 7-oxodesacetoxycephalosporanic acid hydrate. The title compound is obtained from its hydrate as described above.

EXAMPLE 5

When the t-butyl ester of a 7-amino-3-heterocyclicthiomethyl cephalosporin listed below:

7-amino-3-(1-methyltetrazol-5-ylthiomethyl)-3-cephem-4-carboxylic acid
7-amino-3-(4-methyl-1,2,4-triazol-3-ylthiomethyl)-3-cephem-4-carboxylic acid
7-amino-3-(1,3,4-thiadiazol-2-ylthiomethyl)-3-cephem-4-carboxylic acid
7-amino-3-(5-methyl-1,3,4-thiadiazol-2-ylthiomethyl)-3-cephem-4-carboxylic acid
7-amino-3-(1,2,4-thiadiazol-5-ylthiomethyl)-3-cephem-4-carboxylic acid
7-amino-3-(3-methyl-1,2,4-thiadiazol-5-ylthiomethyl)-3-cephem-4-carboxylic acid
7-amino-3-(1,3,4-oxadiazol-2-ylthiomethyl)-3-cephem-4-carboxylic acid
7-amino-3-(5-methyl-1,3,4-oxadiazol-2-ylthiomethyl)-3-cephem-4-carboxylic acid
7-amino-3-(tetrazol-5-ylthiomethyl)-3-cephem-4-carboxylic acid
7-amino-3-(1,2,4-triazol-3-ylthiomethyl)-3-cephem-4-carboxylic acid
7-amino-3-(5-methyl-1,2,4-triazol-3-ylthiomethyl)-3-cephem-4-carboxylic acid
7-amino-3-(1-methyl-1,2,4-triazol-5-ylthiomethyl)-3-cephem-4-carboxylic acid
7-amino-3-(1,2,3-triazol-4-ylthiomethyl)-3-cephem-4-carboxylic acid
7-amino-3-(3-methyl-1,2,3-triazol-4-ylthiomethyl)-3-cephem-4-carboxylic acid
7-amino-3-(5-methyl-1,2,3-triazol-4-ylthiomethyl)-3-cephem-4-carboxylic acid is substituted in the procedure of Example 1 for 7-aminocephalosporanic acid t-butyl ester, the resulting 7-oxo-3-heterocyclicthiomethyl-3-cephem-4-carboxylic acid t-butyl esters listed below are obtained:

7-oxo-3-(1-methyltetrazol-5-ylthiomethyl)-3-cephem-4-carboxylic acid t-butyl ester
7-oxo-3-(4-methyl-1,2,4-triazol-3-ylthiomethyl)-3-cephem-4-carboxylic acid t-butyl ester
7-oxo-3-(1,3,4-thiadiazol-2-ylthiomethyl)-3-cephem-4-carboxylic acid t-butyl ester
7-oxo-3-(5-methyl-1,3,4-thiadiazol-2-ylthiomethyl)-3-cephem-4-carboxylic acid t-butyl ester
7-oxo-3-(1,2,4-thiadiazol-5-ylthiomethyl)-3-cephem-4-carboxylic acid t-butyl ester
7-oxo-3-(3-methyl-1,2,4-thiadiazol-5-ylthiomethyl)-3-cephem-4-carboxylic acid t-butyl ester
7-oxo-3-(1,3,4-oxadiazol-2-ylthiomethyl)-3-cephem-4-carboxylic acid t-butyl ester
7-oxo-3-(5-methyl-1,3,4-oxadiazol-2-ylthiomethyl)-3-cephem-4-carboxylic acid t-butyl ester
7-oxo-3-(tetrazol-5-ylthiomethyl)-3-cephem-4-carboxylic acid t-butyl ester
7-oxo-3-(1,2,4-triazol-3-ylthiomethyl)-3-cephem-4-carboxylic acid t-butyl ester
7-oxo-3-(5-methyl-1,2,4-triazol-3-ylthiomethyl)-3-cephem-4-carboxylic acid t-butyl ester
7-oxo-3-(1-methyl-1,2,4-triazol-5-ylthiomethyl)-3-cephem-4-carboxylic acid t-butyl ester
7-oxo-3-(1,2,3-triazol-4-ylthiomethyl)-3-cephem-4-carboxylic acid t-butyl ester
7-oxo-3-(3-methyl-1,2,3-triazol-4-ylthiomethyl)-3-cephem-4-carboxylic acid t-butyl ester
7-oxo-3-(5-methyl-1,2,3-triazol-4-ylthiomethyl)-3-cephem-4-carboxylic acid t-butyl ester The 7-oxo cephalosporin esters listed above are converted to the corresponding free acids as described in the procedure of Example 3.

In like manner, other 7-amino-3-heterocyclicthiomethyl cephalosporins may be oxidized to the corresponding 7-oxo compounds.

EXAMPLE 6

6-Oxopenicillanic Acid Benzyl Ester

A solution of 3.06 g. (10 mmol.) of 6-aminopenicillanic acid benzyl ester and 2.20 g. (10 mmol.) of 3,5-di-t-butyl-1,2-benzoquinone in 50 ml. of tetrahydrofuran containing 5 g. of 5A molecular sieves is maintained at 4° for 16 hours. The solution is decanted and treated with 3 g. of oxalic acid in 10 ml. of water. After standing at 4° for 6 hours most of the solvent is removed below ambient temperature and the residue is partitioned between benzene and water. The aqueous phase is extracted with additional benzene and the combined organic phases are dried (MgSO$_4$) and evaporated to dryness to give a residue which is chromatographed on silica gel with benzene-ethyl acetate as eluant to give the title compound.

EXAMPLE 7

When a carbonyl-containing oxidizing agent listed below:

3,5-di-i-propyl-1,2-benzoquinone
3-methyl-5-i-propyl-1,2-benzoquinone
tetrachloro-1,2-benzoquinone
tetrabromo-1,2-benzoquinone
2,6-di-t-butyl-1,4-benzoquinone is substituted for 3,5-di-t-butyl-1,2-benzoquinone in the procedure of Example 1, 7-oxodesacetoxycephalosporanic acid t-butyl ester hydrate is obtained.

Similarly, other 7-oxo cephalosporins and 6-oxo penicillins may be prepared from the corresponding 7-amino or 6-amino compounds by use of a carbonyl-containing oxidizing agent listed above.

EXAMPLE 8

A solution of 1.35 g. (5 mmol.) of 7-aminodesacetoxycephalosporanic acid t-butyl ester and 1.33 g. (5 mmol.) of 3,5-dinitromesitylglyoxal in 25 ml. of tetrahydrofuran-dimethylsulfoxide (1:1) containing 2 g. of 5A molecular sieves is stirred at 10° for 2 hours under a nitrogen atmosphere. After addition of 0.35 ml. (2.5 mmol.) of triethylamine, the reaction is allowed to stand for 2 hours. Water (10 ml.) and 3 g. of oxalic acid are added and the mixture is worked up as described in the procedure of Example 1 to give 7-oxodesacetoxycephalosporanic acid t-butyl ester.

Substitution of 3-nitromesitylglyoxal, mesitylglyoxal, 6-nitrobenzothiazole-2-carboxaldehyde or benzothiazole-2-carboxaldehyde in place of 3,5-dinitromesitylglyoxal in the procedure described above also gives 7-oxodesacetoxycephalosporanic acid t-butyl ester as the product.

In a similar manner, other 7-oxo cephalosporins and 6-oxo penicillins may be prepared by reaction of 3,5-dinitromesitylglyoxal or other carbonyl-containing oxidizing agent mentioned above with the corresponding 7-amino or 6-amino compound.

PREPARATION 1

7β-Hydroxycephalosporanic acid

A solution of 1.38 g. (4 mmol.) of 7-oxocephalosporanic acid t-butyl ester hydrate in 50 ml. of isopropanol and 3 ml. of water was cooled to 0° (ice bath) and 0.150 g. (4 mmol.) of sodium borohydride was added with stirring. The reaction mixture was stirred for five minutes then decomposed by addition of acetic acid. The mixture was extracted with ethyl acetate and the organic phase was washed with water, dried (MgSO$_4$) and evaporated to dryness to give a residue which was recrystallized from ethyl acetate-hexane to give 7β-hydroxycephalosporanic acid t-butyl ester.

$C_{14}H_{19}NO_6S \cdot 0.25\ H_2O$: Calculated: 50.36% C; 5.89% H; 4.20% N; Found: 50.64% C; 5.95% H; 4.02% N 7β-Hydroxycephalosporanic acid t-butyl ester (1.0 g.) was stirred in 10 ml. of trifluoroacetic acid containing 1% anisole at 25° for two hours. The reaction mixture was evaporated to dryness, the residue was triturated with ether-hexane and the precipitated product was collected and recrystallized from tetrahydrofuranhexane to give the title compound.

$C_{10}H_{11}NO_6S \cdot 0.66\ C_4H_8O \cdot 0.5\ H_2O$: Calculated: 46.03% C; 5.29% H; 4.26% N; Found: 46.38% C; 5.12% H; 3.90% N

PREPARATION 2

7β-(D-α-aminophenylacetoxy)cephalosporanic acid

To a solution of 0.126 g. (0.5 mmol.) of D-N-t-butoxycarbonylphenylglycine in 10 ml. of tetrahydrofuran at −15° under a nitrogen atmosphere was added 0.075 ml. (0.5 mmol.) of triethylamine followed by 0.039 ml. (0.5 mmol.) of ethyl chloroformate. The mixture was stirred for 15 minutes then a solution of 0.165 g. (0.5 mmol.) of 7β-hydroxycephalosporanic acid t-butyl ester in 25 ml. of tetrahydrofuran was slowly added and the resulting mixture was stirred at 0° for one hour, then at ambient temperature for 12 hours. Water was added to the reaction mixture and it was extracted repeatedly with ether. The combined extracts were washed with saturated sodium chloride solution, dried and evaporated to dryness to give a residue which was chromatographed on silica with benzene-ethyl acetate as eluant to give 7β-(D-α-N-t-butoxycarbonylaminophenylacetoxy)cephalosporanic acid t-butyl ester.

7β-(D-α-N-t-Butoxycarbonylaminophenylacetoxy)cephalosporanic acid t-butyl ester (0.2 g.) was stirred with 20% trifluoroacetic acid in methylene chloride containing anisole at 25° for three hours. The solution was evaporated to dryness and the residue was washed with hexane. Ether was added to the residue to give the title compound.

$C_{18}H_{18}N_2O_7S \cdot 0.3\ CF_3CO_2H$: Calculated: 46.16% C; 3.68% H; 5.38% N; Found: 50.81% C; 4.30% H; 6.35% N

PREPARATION 3

7β-Trifluoromethylthioacetoxycephalosporanic acid

A solution of 0.40 g. (2.5 mmol.) of trifluoromethylthioacetic acid and 0.35 g. (2.75 mmol.) of oxalyl chloride in 3 ml. of benzene was cooled to 0° and 0.20 g. of pyridine in 1 ml. of benzene was added under an argon atmosphere. The reaction mixture was stirred for 15 minutes then filtered. The filtrate was added dropwise to a stirred solution of 0.66 g. (2.0 mmol.) of 7β-hydroxycephalosporanic acid t-butyl ester in 80 ml. of ether containing 0.15 ml. of pyridine at 0°. After addition, the mixture was stirred at 25° for 0.5 hour then ice water was added and the layers were separated. The aqueous phase was thoroughly extracted with ether, and the combined organic phases were washed with saturated sodium chloride solution, dried and evaporated to dryness to give a residue which was chromatographed on silica with benzene-ethyl acetate as eluant to give 7β-trifluoromethylthioacetoxycephalosporanic acid t-butyl ester.

7β-Trifluoromethylthioacetoxycephalosporanic acid t-butyl ester (0.4 g.) was stirred in 10 ml. of trifluoroacetic acid at 25° for three hours. The solution was evaporated to dryness to give the title compound.

$C_{13}H_{12}F_3NO_7S$: Calculated: 37.59% C; 3.06% H; 3.37% N; Found: 37.67% C; 3.06% H; 3.00% N

PREPARATION 4

7β-Phenoxyacetoxycephalosporanic acid

To a solution of 0.448 g. (1.35 mmol.) of 7β-hydroxycephalosporanic acid t-butyl ester and 0.1 ml. of pyridine in 60 ml. of anhydrous ether at 0° was added 0.24 g. (1.4 mmol.) of phenoxyacetylchloride. The reaction mixture was stirred for one hour in the cold then for 30 minutes at ambient temperature. Cold water was added to the mixture, the layers were separated and the aqueous phase was extracted repeatedly with ether. The combined ether layers were washed with saturated sodium chloride solution, dried (Na$_2$SO$_4$) and evaporated to dryness. The residue was chromatographed on silica with benzene-ethyl acetate as eluant to give 7β-phenoxyacetoxycephalosporanic acid t-butyl ester.

$C_{22}H_{25}NO_8S$: Calculated: 57.01% C; 5.44% H; 3.02% N; Found: 57.48% C; 5.54% H; 2.60% N 7β-Phenoxyacetoxycephalosporanic acid t-butyl ester was treated with trifluoroacetic acid as previously described to give the title compound.

$C_{18}H_{17}NO_8S$: Calculated: 53.07% C; 4.21% H; 3.44% N; Found: 53.12% C; 4.30% H; 3.24% N

PREPARATION 5

7β-(D-α-Hydroxyphenylacetoxy)cephalosporanic acid

To a solution of 0.659 g. (2.0 mmol.) of 7β-hydroxycephalosporanic acid t-butyl ester in 60 ml. of methylene chloride containing 0.16 ml. of pyridine at 0° under a nitrogen atmosphere was added 0.600 g. (2.2 mmol.) of D-O-dichloroacetylmandeloyl chloride in 10 ml. of methylene chloride. The reaction mixture was stirred for 30 minutes in the cold, then warmed to ambient temperature and diluted with water. The aqueous phase was thoroughly extracted with methylene chloride. The organic layers were combined, washed with saturated sodium chloride, dried (Na$_2$SO$_4$) and evaporated to dryness to give a residue which was chromatographed on silica with benzene-ethyl acetate as eluant to give 7β-(D-α-dichloroacetoxyphenylacetoxy)cephalosporanic acid t-butyl ester.

7β-(D-α-Dichloroacetoxyphenylacetoxy)cephalosporanic acid t-butyl ester (0.60 g.) was stirred with 50 ml. of 20% trifluoroacetic acid in methylene chloride containing anisole at 25° for two hours. The solution was evaporated to dryness and the residue was washed with hexane and chromatographed on silica with 1% acetic acid in benzene-ethyl acetate as eluant to give 7β-(D-α-dichloroacetoxyphenylacetoxy)cephalosporanic acid.

7β-(D-α-Dichloroacetoxyphenylacetoxy)cephalosporanic acid (0.330 g.) was dissolved in acetone and a solution of 3:1 0.01M Na₂HPO₄:0.1M NaH₂PO₄ buffer was added dropwise until pH 7.2. The solution was allowed to stand for 20 minutes then it was cooled and acidified with dilute phosphoric acid until pH 1.5. The acidic solution was extracted with ether and the extract was washed with saturated sodium chloride solution, dried (MgSO₄) and evaporated to dryness. The residue was crystallized from ethyl acetate-hexane to give the title compound.

PREPARATION 6

6β-Hydroxypenicillanic acid

6-Oxopenicillanic acid benzyl ester is reduced by potassium borohydride in aqueous alcohol according to the procedure of Preparation 1 to give, after chromatography, 6β-hydroxypenicillanic acid benzyl ester.

Removal of the benzyl ester group according to standard procedures gives the title compound.

PREPARATION 7

6β-Phenoxyacetoxypenicillanic acid

Reaction of 6β-hydroxypenicillanic acid benzyl ester with phenoxyacetylchloride as described in Preparation 4 gives 6β-phenoxyacetoxypenicillanic acid benzyl ester.

Removal of the benzyl ester group according to standard procedures gives the title compound.

PREPARATION 8

7β-Hydroxy-3-(1-methyltetrazol-5-ylthiomethyl)-3-cephem-4-carboxylic acid

A. To a suspension of 27.3 g. (0.1 mol.) of 7β-hydroxycephalosporanic acid in 200 ml. of water and 100 ml. of acetone is added a solution of 18.9 g. of sodium bicarbonate in 200 ml. of water. The resultant solution is warmed on a steam bath and a solution of 14.5 g. (0.125 mol.) of 1-methyl-5-mercaptotetrazole in 200 ml. of acetone is added. The reaction mixture is refluxed for 3.5 hours while maintaining the pH at 7.4–8.0 by addition of 5% aqueous sodium bicarbonate. Acidification of the cooled reaction mixture to pH 3.5 with 6N hydrochloric acid and collection of the product gives the title compound.

B. Reaction of 7-oxocephalosporanic acid and 1-methyl-5-mercaptotetrazole according to procedure A above gives 7-oxo-3-(1-methyltetrazol-5-ylthiomethyl)-3-cephem-4-carboxylic acid.

Reduction of 7-oxo-3-(1-methyltetrazol-5-ylthiomethyl)-3-cephem-4-carboxylic acid as described in Preparation 1 gives the title compound.

PREPARATION 9

7β-Trifluoromethylthioacetoxy-3-(5-methyl-1,3,4-thiadiazol-2-ylthiomethyl)-3-cephem-4-carboxylic acid A. Reaction of 7β-trifluoromethylthioacetoxycephalosporanic acid and 2-methyl-5-mercapto-1,3,4-thiadiazole according to the procedure of Preparation 8-A gives the title compound.

B. 7β-Hydroxy-3-(5-methyl-1,3,4-thiadiazol-2-ylthiomethyl)-3-cephem-4-carboxylic acid is prepared from 7-oxo-3-(5-methyl-1,3,4-thiadiazol-2-ylthiomethyl)-3-cephem-4-carboxylic acid as described above.

Reaction of 7β-hydroxy-3-(5-methyl-1,3,4-thiadiazol-2-ylthiomethyl)-3-cephem-4-carboxylic acid and trifluoromethylthioacetic acid according to the procedure of Preparation 3 gives the title compound.

What is claimed is:

1. A process for preparing a compound of the formula:

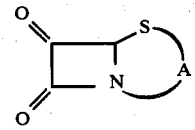

in which:

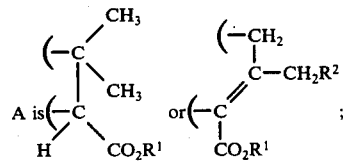

$R^1$ is hydrogen or an easily removable conventional penicillin or cephalosporin ester protecting group; and $R^2$ is hydrogen, acetoxy or SHet where Het is a five or six membered heterocyclic ring containing carbon and one to four atoms selected from the group consisting of N, O and S, each such ring being unsubstituted or substituted with one or two groups selected from alkyl, alkoxyalkyl and trifluoromethyl, each alkyl or alkoxy group having from one to four carbon atoms, comprising reacting, in the presence of a non-hydroxylic solvent, a 7-amino cephalosporin or 6-amino penicillin of the formula:

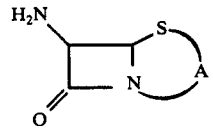

in which A, $R^1$ and $R^2$ are defined as above, with a carbonyl containing oxidizing agent selected from the group consisting of:

mesitylglyoxal,
3-nitromesitylglyoxal,
3,5-dinitromesitylglyoxal,
benzothiazole-2-carboxaldehyde,
6-nitrobenzothiazole-2-carboxaldehyde,
3,5-di-i-propyl-1,2-benzoquinone,
3-methyl-5-i-propyl-1,2-benzoquinone,
tetrachloro-1,2-benzoquinone
tetrabromo-1,2-benzoquinone,
2,6-di-t-butyl-1,4-benzoquinone and
3,5-di-t-butyl-1,2-benzoquinone, said reaction being carried out with removal of water.

2. A process according to claim 1 in which $R^1$ is benzhydryl, t-butyl, 2,2,2-trichloroethyl, benzyl, benzyloxymethyl, p-nitrophenyl, p-methoxyphenyl, p-nitrobenzyl or p-methoxybenzyl.

3. A process according to claim 1 in which $R^2$ is hydrogen, acetoxy or SHet where Het is unsubstituted or methyl substituted 1,2,3-triazolyl, 1,2,4-triazolyl, 1,2,3,4-tetrazolyl, 1,3,4-oxadiazolyl, 1,3,4-thiadiazolyl or 1,2,4-thiadiazolyl.

4. A process according to claim 1 in which the reaction is carried out in tetrahydrofuran, dioxane, chloroform, methylene chloride, carbon tetrachloride, benzene, toluene, xylene, ethyl acetate, ether, acetonitrile, dimethylformamide or dimethylsulfoxide.

5. A process according to claim 4 in which the carbonyl-containing oxidizing agent is 3,5-di-t-butyl-1,2-benzoquinone.

6. A process according to claim 4 in which the 7-amino cephalosporin or 6-amino penicillin and the carbonyl-containing oxidizing agent are present in equimolar amounts.

7. A process according to claim 6 in which the reaction is carried out in the presence of a dehydrating agent.

8. A process according to claim 6 in which the reaction is carried out with azeotropic removal of water.

9. A process according to claim 6 in which the reaction is base catalyzed.

10. A process according to claim 7 in which the reaction is carried out at a temperature of from about 0° C. to about 190° C. for from about 1 to about 72 hours.

11. A process according to claim 10 in which the reaction is carried out at a temperature of from about 0° C. to about 25° C. for from about 12 to about 72 hours.

12. A process according to claim 11 for preparing 7-oxocephalosporanic acid t-butyl ester comprising reacting 7-aminocephalosporanic acid t-butyl ester with 3,5-di-t-butyl-1,2-benzoquinone in tetrahydrofuran in the presence of molecular sieves as a dehydrating agent at 4° C. for 12 hours.

13. A process according to claim 11 for preparing 7-oxodesacetoxycephalosporanic acid t-butyl ester comprising reacting 7-aminodesacetoxycephalosporanic acid t-butyl ester and 3,5-di-t-butyl-1,2-benzoquinone in tetrahydrofuran in the presence of molecular sieves as a dehydrating agent at 4° C. for 72 hours.

14. A process according to claim 11 for preparing 7-oxodesacetoxycephalosporanic acid comprising reacting 7-aminodesacetoxycephalosporanic acid and 3,5-di-t-butyl-1,2-benzoquinone in acetonitrile in the presence of anhydrous magnesium sulfate as a dehydrating agent at 4° C. for 20 hours.

15. A process according to claim 11 for preparing 6-oxopenicillanic acid benzyl ester comprising reacting 6-aminopenicillanic acid benzyl ester and 3,5-di-t-butyl-1,2-benzoquinone in tetrahydrofuran in the presence of molecular sieves as a dehydrating agent at 4° C. for 16 hours.

* * * * *